US011643551B2

(12) United States Patent
Al-Rashid et al.

(10) Patent No.: US 11,643,551 B2
(45) Date of Patent: May 9, 2023

(54) SYNTHETIC MEMBRANE COMPOSITION COMPRISING A POLYURETHANE AND A POLYOXAZOLINE

(71) Applicant: DSM IP Assets B.V., Heerlen (NL)

(72) Inventors: Jennifer Al-Rashid, Exton, PA (US); Jacob Riffey, Exton, PA (US); Chad Sugiyama, Exton, PA (US); John Zupancich, Exton, PA (US)

(73) Assignee: DSM IP ASSETS B.V., Heerlen (NL)

( * ) Notice: Subject to any disclaimer, the term of this patent is extended or adjusted under 35 U.S.C. 154(b) by 417 days.

(21) Appl. No.: 16/642,053

(22) PCT Filed: Aug. 28, 2018

(86) PCT No.: PCT/US2018/048315
§ 371 (c)(1),
(2) Date: Feb. 26, 2020

(87) PCT Pub. No.: WO2019/046284
PCT Pub. Date: Mar. 7, 2019

(65) Prior Publication Data
US 2021/0070989 A1  Mar. 11, 2021

Related U.S. Application Data

(60) Provisional application No. 62/550,922, filed on Aug. 28, 2017, provisional application No. 62/550,937, filed on Aug. 28, 2017, provisional application No. 62/550,929, filed on Aug. 28, 2017.

(30) Foreign Application Priority Data

Sep. 15, 2017 (EP) .................................. 17191475
Sep. 15, 2017 (EP) .................................. 17191476
Sep. 15, 2017 (EP) .................................. 17191477

(51) Int. Cl.
| | |
|---|---|
| C08L 75/08 | (2006.01) |
| A61B 5/145 | (2006.01) |
| A61B 5/1473 | (2006.01) |
| B01D 67/00 | (2006.01) |
| B01D 69/02 | (2006.01) |
| B01D 71/54 | (2006.01) |
| B01D 71/58 | (2006.01) |
| C08G 18/24 | (2006.01) |
| C08G 18/28 | (2006.01) |
| C08G 18/48 | (2006.01) |
| C08G 18/66 | (2006.01) |
| C08G 18/73 | (2006.01) |
| C08G 18/75 | (2006.01) |
| C08J 5/18 | (2006.01) |
| C12Q 1/00 | (2006.01) |

(52) U.S. Cl.
CPC .......... *C08L 75/08* (2013.01); *A61B 5/14532* (2013.01); *A61B 5/14735* (2013.01); *B01D 67/0011* (2013.01); *B01D 67/0095* (2013.01); *B01D 69/02* (2013.01); *B01D 71/54* (2013.01); *B01D 71/58* (2013.01); *C08G 18/244* (2013.01); *C08G 18/283* (2013.01); *C08G 18/2825* (2013.01); *C08G 18/4808* (2013.01); *C08G 18/4833* (2013.01); *C08G 18/4854* (2013.01); *C08G 18/6674* (2013.01); *C08G 18/73* (2013.01); *C08G 18/755* (2013.01); *C08G 18/758* (2013.01); *C08J 5/18* (2013.01); *C12Q 1/00* (2013.01); *A61B 5/14546* (2013.01); *B01D 2323/12* (2013.01); *B01D 2325/34* (2013.01); *B01D 2325/36* (2013.01); *C08J 2375/08* (2013.01); *C08J 2475/04* (2013.01); *C08L 2203/16* (2013.01); *C08L 2205/025* (2013.01)

(58) Field of Classification Search
CPC ........ B01D 71/54; B01D 69/02; B01D 71/58; C08L 2203/16; C08L 2205/025; C08L 75/04; C08L 83/04
See application file for complete search history.

(56) References Cited

U.S. PATENT DOCUMENTS

| | | | |
|---|---|---|---|
| 4,686,137 A | 8/1987 | Ward, Jr. | |
| 5,378,268 A * | 1/1995 | Wolf ....................... | C23C 18/28 |
| | | | 106/1.11 |
| 5,589,563 A | 12/1996 | Ward | |

(Continued)

FOREIGN PATENT DOCUMENTS

| | | | |
|---|---|---|---|
| CN | 1371927 A | * | 10/2002 |
| EP | 2295132 A1 | | 3/2011 |

(Continued)

OTHER PUBLICATIONS

Hartlieb et al. (J. Mater. Chem. B, 2015, 3, 526) "Covalently cross-linked poly(2-oxazoline) materials for biomedical applications—from hydrogels to self-assembled and templated structures" (Year: 2015).*
Polysciences (Poly(2-ethyl-2-oxazoline) [MW 200,000], Product Page, Polysciences). URL: https://www.polysciences.com/default/poly2-ethyl-2-oxazoline-mw-200000, accessed Jul. 30, 2022 (Year: 2022).*
International Search Report, dated Nov. 19, 2018.

(Continued)

*Primary Examiner* — Ryan B Huang
(74) *Attorney, Agent, or Firm* — Kevin M. Bull

(57) ABSTRACT

Disclosed are compositions that may be useful for forming synthetic membranes, methods of forming membranes therefrom, and membranes. In an embodiment, a membrane comprises a free hydrophilic polymer comprising a polyoxazoline, and a polyurethane, the polyurethane comprising a backbone comprising the reaction product of a diisocyanate, a polymeric aliphatic 5 diol, and optionally a chain extender.

20 Claims, No Drawings

(56) References Cited

U.S. PATENT DOCUMENTS

| | | |
|---|---|---|
| 7,157,528 B2 | 1/2007 | Ward |
| 7,226,978 B2 | 6/2007 | Tapsak et al. |
| 7,459,167 B1 * | 12/2008 | Sengupta ............ C08F 290/067 424/78.37 |
| 7,687,586 B2 | 3/2010 | Ward |
| 3,050,731 A1 | 11/2011 | Fapsak |
| 8,255,032 B2 | 8/2012 | Petisce |
| 8,865,249 B2 | 10/2014 | Fapsak |
| 9,414,778 B2 | 8/2016 | Mao |
| 2003/0157277 A1 | 8/2003 | Romano et al. |
| 2003/0217966 A1 | 11/2003 | Tapsak et al. |
| 2006/0258761 A1 | 11/2006 | Boock et al. |
| 2007/0197889 A1 | 8/2007 | Brister et al. |
| 2010/0200541 A1 | 8/2010 | Habassi et al. |
| 2011/0031100 A1 | 2/2011 | Qtaishat et al. |
| 2011/0152654 A1 | 6/2011 | Wang et al. |
| 2012/0021147 A1 | 1/2012 | Liao |

FOREIGN PATENT DOCUMENTS

| | | |
|---|---|---|
| EP | 3496845 A1 | 6/2019 |
| JP | 2004300178 A * | 10/2004 |
| JP | 2014138881 A | 7/2014 |
| WO | 03100083 A1 | 12/2003 |
| WO | WO2018029131 A1 | 2/2018 |
| WO | WO2019046279 A1 | 3/2019 |
| WO | WO2019046281 A1 | 3/2019 |
| WO | WO2019046284 A1 | 3/2019 |

OTHER PUBLICATIONS

Kim, et al., Preparation of Water Repellent Polyurethane Coating Films Using Perfluoroalkyl Alcohol, Korean Chem Eng. Res., 54(3), 387-393 (2016).

M. Khayet, et al., Study on Surface Modification by Surface-Modifying Macromolecules and its Applications in Membrane-Separation Processes, Journal of Applied Polymer Science, vol. 89, 2902-2916, 2003.

\* cited by examiner

SYNTHETIC MEMBRANE COMPOSITION COMPRISING A POLYURETHANE AND A POLYOXAZOLINE

CROSS-REFERENCE TO RELATED APPLICATIONS

This application is a U.S. national phase entry under 35 USC 371 of international application PCT/US2018/048315, which designated the U.S. and claims priority to U.S. Provisional Application 62/550,922, filed 28 Aug. 2017, U.S. Provisional Application 62/550,929, filed 28 Aug. 2017, U.S. Provisional Application 62/550,937, filed 28 Aug. 2017, European Patent Application EP17191475.7, filed 15 Sep. 2017, European Patent Application EP17191476.5, filed 15 Sep. 2017, and European Patent Application EP17191477.3, filed 15 Sep. 2017, the entire contents of each of which is hereby incorporated by reference in its entirety.

FIELD

The disclosed inventions pertain to compositions that may be useful for forming synthetic membranes, methods of forming membranes therefrom, and membranes.

BACKGROUND

A sensor may comprise an analyte diffusion-limiting membrane. Without an analyte diffusion-limiting membrane, a sensor becomes saturated quickly and at low analyte concentrations. Ideally, a sensor has sufficient oxygen for adequate operation, but saturation of the target analyte at the sensor surface is prevented. An oxygen permeable membrane that restricts analyte flux to the sensing layer is thus often required. Preferred diffusion-limiting membranes are mechanically strong, biocompatible, minimize protein adsorption, have sufficient oxygen diffusivity, and are easily manufactured.

Synthetic membranes formed from polyurethanes are known. Polyurethanes have been chosen due to their ability to form films when blended with a range of solvents and ability to regulate the flux of analytes to sensors.

For instance, U.S. Pat. No. 5,589,563 discloses the casting of membranes from polyurethanes comprising surface modifying endgroups. A polyurethane with a surface modifying endgroups is a polyurethane comprising one or more endgroups at the terminal ends of the backbone of the polyurethane. The surface modifying endgroups and backbone are such that the surface activity of such a polyurethane reflects the surface activity of the surface modifying endgroups rather than the backbone.

Further techniques for forming membranes from polyurethanes are disclosed in U.S. Pat. No. 7,226,978. A membrane formed from a blend of amphiphilic copolymer and hydrophobic polymer is disclosed. It is stated that the blend allows membranes having hydrophilic domains that control the diffusion of an analyte therethrough dispersed in a hydrophobic matrix. Polyurethanes may be employed as the amphiphilic copolymer or hydrophobic polymer.

Another technique for forming membranes is disclosed in U.S. Pat. Nos. 7,157,528 and 7,687,586. In these documents a biocompatible multipolymer is disclosed. The multipolymer comprises a hydrophilic soft segment and an oxygen-permeable soft segment.

Further techniques for forming membranes from polyurethanes are disclosed in U.S. Pat. No. 8,255,032. A membrane comprising a blend of silicone-containing polyurethane with hydrophilic polymer is disclosed. The hydrophilic polymer may be polyvinylpyrrolidone, polyhydroxyethyl methacrylate, polyvinylalcohol, polyacrylic acid, polyethers, and copolymers thereof.

Despite these documents, there is still a need for compositions for forming synthetic membranes that yield suitable mechanical properties and film quality, in a more reproducible process.

SUMMARY

Known compositions for forming synthetic membranes may be deficient in desired performance and processing characteristics. For example, forming films from a blend of a hydrophilic polymer, such as PVP, and a hydrophobic polyurethane may present difficulty in reproducibility due to microphase separation of the dissimilar polymers. Furthermore, such membranes may suffer from reduced analyte diffusivity. These difficulties can be overcome by using strong, high boiling point organic solvents, such as dimethylacetamide (DMAc) or dimethylformamide (DMF), but this may present health and safety concerns because such solvents are not easily removed from the polymers. Furthermore, certain solvents may dissolve polymer layers on a sensor, restricting their use in certain sensor-related applications.

In an embodiment, a composition for forming a membrane comprises from 90 to 99.5 wt %, based on the total weight of the composition, of a solvent and from 0.5 to 10 wt %, based on the total weight of the composition, of a polymer mixture, the polymer mixture comprising from 60 to 99.5 wt %, based on the total weight of the polymer mixture, of a polyurethane and from 0.5 to 40 wt %, based on the total weight of the polymer mixture, of a free hydrophilic polymer comprising a polyoxazoline, wherein the polyurethane comprises a backbone comprising the reaction product of a diisocyanate, a polymeric aliphatic diol, and optionally a chain extender.

In an embodiment, a membrane comprises:
a. a free hydrophilic polymer comprising a polyoxazoline, and
b. a polyurethane, the polyurethane comprising a backbone comprising the reaction product of a diisocyanate, a polymeric aliphatic diol, and optionally a chain extender.

The compositions, methods, membranes, and articles disclosed herein may exhibit benefits in film formation, reproducibility, mechanical properties, anti-fouling, health and safety, improved compatibility with sensors, and/or solvent removal.

DETAILED DESCRIPTION

In accordance with an embodiment, a composition for forming a membrane comprises from 90 to 99.5 wt %, based on the total weight of the composition, of a solvent and from 0.5 to 10 wt %, based on the total weight of the composition, of a polymer mixture, the polymer mixture comprising from 60 to 99.5 wt %, based on the total weight of the polymer mixture, of a polyurethane and from 0.5 to 40 wt %, based on the total weight of the polymer mixture, of a free hydrophilic polymer, wherein the polyurethane comprises a backbone comprising the reaction product of a diisocyanate, a polymeric aliphatic diol, and optionally a chain extender. In an embodiment, a membrane is formed from the composition.

In an embodiment, a membrane comprises: a) a free hydrophilic polymer comprising a polyoxazoline, and a polyurethane. The polyurethane comprises a backbone comprising the reaction product of a diisocyanate, a polymeric aliphatic diol, and optionally a chain extender. In an embodiment, the membrane comprises from 60 to 99.5 wt %, based on the total weight of the membrane, of the polyurethane and from 0.5 to 40 wt %, based on the total weight of the membrane, of the free hydrophilic polymer.

By a reaction product it is meant that the diisocyanate and polymeric aliphatic diol, and optionally the chain extender, are engaged in a simultaneous or sequential chemical reaction. For example, a reaction product of a diisocyanate, a polymeric aliphatic diol, and a chain extender is formed i) when the diisocyanate, polymeric aliphatic diol, and chain extender are all reacted together in a single solution, or ii) when a pre-polymer is first formed by reacting the diisocyanate and the polymeric aliphatic diol, and then this prepolymer is subsequently reacted with the chain extender.

In an embodiment, the polymer mixture in the composition or the membrane comprises from 70 to 99.5 wt % of the polyurethane and from 0.5 to 30 wt % of the free hydrophilic polymer.

In an embodiment, the polymer mixture in the composition or the membrane comprises from 80 to 99.5 wt % of the polyurethane and from 0.5 to 20 wt % of the free hydrophilic polymer. In an embodiment, the polymer mixture in the composition or the membrane comprises from 85 to 99.5 wt % of the polyurethane and from 0.5 to 15 wt % of the free hydrophilic polymer. In an embodiment, the polymer mixture in the composition or the membrane comprises from 90 to 99.5 wt % of the polyurethane and from 0.5 to 10 wt % of the free hydrophilic polymer.

The disclosed compositions, membranes, and sensors may have advantages over the prior art in terms of mechanical properties, such as modulus, tensile strength, elongation, or durability, analyte permeability, oxygen permeability, isotropy of mechanical properties, surface quality, use with a wider range of solvents, process reproducibility, process speed, health and safety concerns, such as easier or more expedient removal of residual solvent.

Free Hydrophilic Polymer

The membrane or composition for forming a membrane comprises a free hydrophilic polymer comprising a polyoxazoline. A free hydrophilic polymer is a hydrophilic polymer that is not bound to the polyurethane by covalent bonds. In an embodiment, the free hydrophilic polymer consists of a polyoxazoline. In an embodiment, the free hydrophilic polymer comprises a poly(2-methyl-2-oxazoline) or a poly(2-ethyl-2-oxazoline). In an embodiment, the free hydrophilic polymer consists of a poly(2-methyl-2-oxazoline), a poly(2-ethyl-2-oxazoline), a mixture thereof, or a copolymer thereof.

In an embodiment, the free hydrophilic polymer comprises a polyoxazoline and one or more of a poly(ethylene oxide), polyvinylpyrrolidone, polyacrylic acid, polyvinyl alcohol, or hyaluronic acid. In an embodiment, the free hydrophilic polymer comprises a polyoxazoline and a polyvinylpyrrolidone.

In an embodiment, the free hydrophilic polymer has a number average molecular weight of at least 5,000 g/mol, at least 10,000 g/mol, at least 50,000 g/mol, at least 100,000 g/mol, or at least 200,000 g/mol. In an embodiment, the free hydrophilic polymer has a number average molecular weight of at most 10,000,000 g/mol, at most 5,000,000 g/mol, at most 2,000,000 g/mol, at most 1,000,000 g/mol, at most 500,000 g/mol, or at most 200,000 g/mol.

Polyurethane

The polyurethane comprises a backbone that comprises the reaction product of a diisocyanate, a polymeric aliphatic diol, and optionally a chain extender. In an embodiment, the polyurethane consists of a backbone that comprises the reaction product of a diisocyanate, a polymeric aliphatic diol, and optionally a chain extender. In an embodiment, the polyurethane further comprises an endgroup. In an embodiment, the polyurethane is linear. In an embodiment, the polyurethane is branched.

In an embodiment, the polyurethane backbone, endgroup, or both comprise a $C_2$-$C_{16}$ fluoroalkyl or $C_2$-$C_{16}$ fluoroalkyl ether. By comprises a $C_2$-$C_{16}$ fluoroalkyl or $C_2$-$C_{16}$ fluoroalkyl ether it is meant that a $C_2$-$C_{16}$ fluoroalkyl or $C_2$-$C_{16}$ fluoroalkyl ether moiety is present. In an embodiment, the backbone comprises a $C_2$-$C_{16}$ fluoroalkyl or $C_2$-$C_{16}$ fluoroalkyl ether. In an embodiment, the endgroup comprises a $C_2$-$C_{16}$ fluoroalkyl or $C_2$-$C_{16}$ fluoroalkyl ether. In an embodiment, the polyurethane comprises an average of at least 0.1 endgroups, at least 0.25 endgroups, at least 0.5 endgroups, at least 1 endgroup, at least 1.5 endgroups, at least 1.8 endgroups, about 2 endgroups, or at least 2 endgroups comprising a $C_2$-$C_{16}$ fluoroalkyl or $C_2$-$C_{16}$ fluoroalkyl ether. In an embodiment, both the backbone and the endgroup comprise a $C_2$-$C_{16}$ fluoroalkyl or $C_2$-$C_{16}$ fluoroalkyl ether.

In an embodiment, the polyurethane backbone comprises a $C_2$-$C_{16}$ fluoroalkyl or $C_2$-$C_{16}$ fluoroalkyl ether. The $C_2$-$C_{16}$ fluoroalkyl or $C_2$-$C_{16}$ fluoroalkyl ether may be incorporated into the backbone by incorporating a diol comprising $C_2$-$C_{16}$ fluoroalkyl or $C_2$-$C_{16}$ fluoroalkyl ether in the formulation from which the polyurethane is formed. In an embodiment, the polyurethane backbone comprises the residue of 1H,1H,4H,4H-Perfluoro-1,4-butanediol, 1H,1H,5H,5H-Perfluoro-1,5-pentanediol, 1H,1H,6H,6H-perfluoro-1,6-hexanediol, 1H,1H,8H,8H-Perfluoro-1,8-octanediol, 1H,1H,9H,9H-Perfluoro-1,9-nonanediol, 1H,1H,10H,10H-Perfluoro-1,10-decanediol, 1H,1H,12H,12H-Perfluoro-1,12-dodecanediol, 1H,1H,8H,8H-Perfluoro-3,6-dioxaoctan-1,8-diol, 1H,1H,11H,11H-Perfluoro-3,6,9-trioxaundecan-1,11-diol. fluorinated triethylene glycol, or fluorinated tetraethylene glycol.

In an embodiment, the polyurethane backbone comprises a block comprising fluoroalkyl or fluoroalkyl ether having an Mn of at least 150 g/mol, at least 250 g/mol, or at least 500 g/mol. In an embodiment, the pre-polymer comprises a block comprising fluoroalkyl or fluoroalkyl ether having a Mn of at most 1500 g/mol, at most 1000 g/mol, or at most 850 g/mol.

In an embodiment, the polyurethane comprises at least 1 wt %, at least 2 wt %, or at least 5 wt % of $C_2$-$C_{16}$ fluoroalkyl or $C_2$-$C_{16}$ fluoroalkyl ether, based on the total weight of the polyurethane. In an embodiment, the polyurethane comprises at most 15 wt %, at most 10 wt %, or at most 8 wt % of $C_2$-$C_{16}$ fluoroalkyl or $C_2$-$C_{16}$ fluoroalkyl ether, based on the total weight of the polyurethane.

In an embodiment, the polyurethane backbone, endgroup, or both comprise a polysiloxane. By comprises a polysiloxane it is meant that a polysiloxane moiety is present. In an embodiment, the backbone comprises a polysiloxane. In an embodiment, the endgroup comprises a polysiloxane. In an embodiment, the polyurethane backbone is substantially devoid of or devoid of polysiloxane moieties. In an embodiment, the polyurethane is substantially devoid of or devoid of endgroups comprising polysiloxane moieties.

In an embodiment, the polyurethane comprises at least 5 wt %, at least 10 wt %, or at least 15 wt % of polysiloxane, based on the total weight of the polyurethane. In an embodiment, the polyurethane comprises at most 50 wt %, at most 40 wt %, or at most 30 wt % of polysiloxane, based on the total weight of the polyurethane.

In an embodiment, the polyurethane is devoid of a hydrophilic polymer moiety. Examples of hydrophilic polymer moieties are polyethylene oxide or polyoxazoline moieties.

Diisocyanate Component

The backbone of the polyurethane comprises the residue of a diisocyanate. In an embodiment, the diisocyanate comprises an average of at least 1.9 isocyanate groups per molecule and an average of less than 2.7 isocyanate groups per molecule.

In an embodiment, the diisocyanate is aliphatic. In an embodiment, the diisocyanate is aromatic. In an embodiment, the diisocyanate comprises 4,4'-diphenylmethane diisocyanate (MDI), 2,4-toluene diisocyanate, 2,6-toluene diisocyanate, 1,4-phenylene diisocyanate, hexamethylene diisocyanate (HDI), tetramethylene-1,4-diisocyanate, cyclohexane-1,4-diisocyanate, dicyclohexylmethane-4,4'-diisocyanate (HMDI), isophorone diisocyanate (IPDI), or a mixture thereof. In an embodiment, the diisocyanate comprises hexamethylene diisocyanate, dicyclohexylmethane 4,4'-diisocyanate, isophorone diisocyanate, or a mixture thereof. In an embodiment, the diisocyanate consists of hexamethylene diisocyanate, dicyclohexylmethane 4,4'-diisocyanate, isophorone diisocyanate, or a mixture thereof. In an embodiment, the diisocyanate comprises 4,4'-diphenylmethane diisocyanate (MDI), 2,4-toluene diisocyanate, 2,6-toluene diisocyanate, or 1,4-phenylene diisocyanate. In an embodiment, the diisocyanate consists of 4,4'-diphenylmethane diisocyanate (MDI), 2,4-toluene diisocyanate, 2,6-toluene diisocyanate, 1,4-phenylene diisocyanate, or a mixture thereof.

In an embodiment, the molecular weight of the diisocyanate is from 100 to 500 g/mol. In an embodiment, the molecular weight of the diisocyanate is from 150 to 260 g/mol.

In an embodiment, the formulation from which the polyurethane is formed comprises at least 10 wt %, at least 20 wt %, at least 25 wt %, at least 30 wt %, at least 35 wt %, or at least 40 wt % of a diisocyanate, based on the total weight of the formulation. In an embodiment, the formulation from which the polyurethane is formed comprises at most 50 wt %, at most 40 wt %, at most 35 wt %, at most 30 wt %, at most 25 wt %, or at most 20 wt % of a diisocyanate, based on the total weight of the formulation. In an embodiment, the polyurethane comprises at least 10 wt %, at least 20 wt %, at least 25 wt %, at least 30 wt %, at least 35 wt %, or at least 40 wt % of the residue of a diisocyanate, based on the polyurethane. In an embodiment, the polyurethane comprises at most 50 wt %, at most 40 wt %, at most 35 wt %, at most 30 wt %, at most 25 wt %, or at most 20 wt % of the residue of a diisocyanate, based on the total weight of the polyurethane.

Polymeric Aliphatic Diol

The polyurethane comprises the residue of a polymeric aliphatic diol. A polymeric aliphatic diol comprises two OH groups and a backbone. The OH groups may be directly attached to the backbone or may be separated by a linker. For example, a hydroxyalkyl terminated polydimethylsiloxane (carbinol terminated) is a polymeric aliphatic diol.

In an embodiment, the polymeric aliphatic diol comprises a poly(alkylene oxide), a polycarbonate, a polysiloxane, a random or block copolymer thereof, or a mixture thereof. In an embodiment, the polymeric aliphatic diol comprises a poly(alkylene oxide), a polycarbonate, a random or block copolymer thereof, or a mixture thereof. In an embodiment, the polymeric aliphatic diol comprises $C_2$-$C_{16}$ fluoroalkyl or $C_2$-$C_{16}$ fluoroalkyl ether.

In an embodiment, the polymeric aliphatic diol comprises a poly(ethylene oxide) diol, a poly(propylene oxide) diol, a poly(tetramethylene oxide) diol, a poly(isobutylene) diol, a polyester diol, for example a polyester diol formed from adipic acid or isophtalic acid and a monomeric diol, an alkane diol, such as a hydrogenated polybutadiene diol or a polyethylene diol, a poly(hexamethylene carbonate) diol, a poly(polytetrahydrofuran carbonate) diol, a polysiloxane diol, a random or block copolymer diol of poly(ethylene oxide) and poly(propylene oxide), a random or block copolymer diol of poly(ethylene oxide) and poly(tetramethylene oxide), a random or block copolymer diol of poly(ethylene oxide) and a polysiloxane, or a mixture thereof.

In an embodiment, the polymeric aliphatic diol comprises a poly(ethylene oxide) diol, a poly(propylene oxide) diol, a poly(tetramethylene oxide) diol, a poly(isobutylene) diol, a polysiloxane diol, a random or block copolymer diol of poly(ethylene oxide) and poly(propylene oxide), a random or block copolymer diol of poly(ethylene oxide) and poly(tetramethylene oxide), a random or block copolymer diol of poly(ethylene oxide) and a polysiloxane, a random or block copolymer diol comprising a polysiloxane or a mixture thereof.

In an embodiment, the polymeric aliphatic diol comprises a mixture of a polysiloxane diol and one or more of a poly(ethylene oxide) diol, a poly(propylene oxide) diol, a poly(tetramethylene oxide) diol, a random or block copolymer diol of poly(ethylene oxide) and poly(propylene oxide), and a random or block copolymer diol of poly(ethylene oxide) and poly(tetramethylene oxide). In an embodiment, the polymeric aliphatic diol comprises a polycarbonate diol that comprises a poly(hexamethylene carbonate) diol or a poly(polytetrahydrofuran carbonate) diol. In an embodiment, the polymeric aliphatic diol consists of polycarbonate diols. In an embodiment, the polymeric aliphatic diol consists of a poly(hexamethylene carbonate) diol, a poly(polytetrahydrofuran carbonate) diol, or a mixture thereof. In an embodiment, the polymeric aliphatic diol comprises a polycarbonate diol having a Mn of at least 500 g/mol, at least 750 g/mol, at least 1000 g/mol, or at least 1500 g/mol. In an embodiment, the polymeric aliphatic diol comprises a polycarbonate diol having a Mn of at most 10,000 g/mol, at most 7500 g/mol, at most 5000 g/mol, at most 4000 g/mol, at most 3000 g/mol, or at most 2500 g/mol.

In an embodiment, the polymeric aliphatic diol comprises a polysiloxane diol, a polycarbonate diol, or a poly(tetramethylene oxide) diol. In an embodiment, the polymeric aliphatic diol consists of a polysiloxane diol, a polycarbonate diol, a poly(tetramethylene oxide) diol, or a mixture thereof. In an embodiment, the polymeric aliphatic diol comprises a mixture of two or more of a polysiloxane diol, a polycarbonate diol, or a poly(tetramethylene oxide) diol. In an embodiment, the polymeric aliphatic diol consists of a mixture of two or more of a polysiloxane diol, a polycarbonate diol, or a poly(tetramethylene oxide) diol. In an embodiment, the polymeric aliphatic diol comprises a polysiloxane diol and one or more of a polycarbonate diol and a poly(tetramethylene oxide) diol. In an embodiment, the polymeric aliphatic diol consists of a polysiloxane diol and one or more of a polycarbonate diol and a poly(tetramethylene oxide) diol. In an embodiment, the polymeric aliphatic diol comprises 15 wt % or less, 10 wt % or less, 5 wt % or less, 2 wt % or less, based on the total weight of polymeric aliphatic diol, or is devoid of hydrophobic poly(alkylene oxide). Hydrophobic poly(alkylene oxide)s are poly(propylene oxide), and poly(tetramethylene oxide). In an embodiment, the polymeric aliphatic diol comprises 15 wt % or less, 10 wt % or less, 5 wt % or less, 2 wt % or less, based on the total weight of polymeric aliphatic diol, or is devoid of polysiloxane. An example of a polysiloxane is polydimethylsiloxane. In an embodiment, the polymeric aliphatic diol comprises 15 wt % or less, 10 wt % or less, 5 wt % or less, 2 wt % or less, based on the total weight of polymeric aliphatic diol, or is devoid of, hydrophobic poly(alkylene oxide) and polysiloxane.

In an embodiment, the polymeric aliphatic diol has a Mn of at least 200 g/mol, at least 250 g/mol, at least 300 g/mol, at least 400 g/mol, or at least 500 g/mol, at least 600 g/mol, at least 700 g/mol, at least 800 g/mol, at least 900 g/mol, or at least 1000 g/mol. In an embodiment, the polymeric aliphatic diol has a Mn of at most 10,000 g/mol, at most 8500 g/mol, at most 6000 g/mol, at most 5000 g/mol, at most 4000 g/mol, at most 3000 g/mol, at most 2000 g/mol, or at most 1500 g/mol.

In an embodiment, the polyurethane is formed from a formulation that comprises at least 20 wt %, at least 30 wt %, at least 40 wt %, at least 50 wt %, or at least 60 wt % of a polymeric aliphatic diol, based on the total weight of the formulation. In an embodiment, the polyurethane is formed from a formulation that comprises at most 80 wt %, at most 70 wt %, at most 60 wt %, or at most 50 wt % of a polymeric aliphatic diol, based on the total weight of the formulation. In an embodiment, the polyurethane comprises at least 20 wt %, at least 30 wt %, at least 40 wt %, at least 50 wt %, or at least 60 wt % of the residue of a polymeric aliphatic diol, based on the total weight of the polyurethane. In an embodiment, the polyurethane comprises at most 80 wt %, at most 70 wt %, at most 60 wt %, or at most 50 wt % of the residue of a polymeric aliphatic diol, based on the total weight of the polyurethane.

Chain Extender

The polyurethane may comprise the residue of a chain extender. A chain extender is an alkane diol having from 2 to 20 carbon atoms, wherein one or more carbon atoms may be substituted with oxygen. In an embodiment, the chain extender has a molecular weight of at least 60 g/mol, at least 70 g/mol, at least 80 g/mol, at least 90 g/mol, or at least 100 g/mol. In an embodiment, the chain extender has a molecular weight of at most 500 g/mol, at most from 400 g/mol, at most 300 g/mol, at most 200 g/mol, or at most 150 g/mol. In an embodiment, the chain extender comprises ethylene glycol, diethylene glycol, propylene glycol, dipropylene glycol, 1,3-propanediol, 1,4-butanediol, 1,5-pentanediol, 1,6-hexanediol, or 1,8-octanediol.

In an embodiment, the polyurethane is formed from a formulation that comprises at least 1 wt %, at least 2 wt %, at least 5 wt %, at least 8 wt %, or at least 10 wt % of a chain extender, based on the total weight of the formulation. In an embodiment, the polyurethane is formed from a formulation that comprises at most 20 wt %, at most 15 wt %, at most 12 wt %, at most 10 wt %, at most 8 wt %, or at most 5 wt %, of a chain extender, based on the total weight of the formulation. In an embodiment, the polyurethane comprises at least 1 wt %, at least 2 wt %, at least 5 wt %, at least 8 wt %, or at least 10 wt % of the residue of a chain extender, based on the total weight of the polyurethane. In an embodiment, the polyurethane comprises at most 20 wt %, at most 15 wt %, at most 12 wt %, at most 10 wt %, at most 8 wt %, or at most 5 wt %, of the residue of a chain extender, based on the total weight of the polyurethane.

Endgroups

In an embodiment, the polyurethane comprises one or more endgroups. An endgroup is a moiety present at a terminal end of a molecule. In an embodiment, the polyurethane is linear and comprises an endgroup at each terminus of the backbone. In an embodiment, the endgroup is linear. In an embodiment, the endgroup is branched. In an embodiment, the polyurethane comprises an average of at least 0.1 endgroups, at least 0.25 endgroups, at least 0.5 endgroups, at least 1 endgroup, at least 1.5 endgroups, at least 1.8 endgroups, about 2 endgroups, or at least 2 endgroups. In an embodiment, the polyurethane comprises an average of at most 4 endgroups an average of at most 2 endgroups, or an average of at most 2 endgroups.

An endgroup may be formed by reacting a terminal isocyanate group present after forming the polymer backbone with a coreactive group on a monofunctional moiety. For instance, a terminal isocyanate group may be reacted with 1-octanol or octylamine to form a $C_8$ alkyl endgroup. Endgroups may also result from the inclusion of chain stoppers, such as monofunctional alcohols, in a formulation used in the formation of a polyurethane. For instance, a formulation for forming a polyurethane may comprise a diisocyanate, a polymeric aliphatic diol, a chain extender, and a monofunctional alcohol.

In an embodiment, the endgroup comprises a hydrophobic poly(alkylene oxide), a hydrophilic poly(alkylene oxide), a copolymer comprising a hydrophilic poly(alkylene oxide) and a hydrophobic poly(alkylene oxide), a polysiloxane, $C_2$-$C_{20}$ alkyl, $C_2$-$C_{16}$ fluoroalkyl, $C_2$-$C_{16}$ fluoroalkyl ether, or copolymers thereof. In an embodiment, the polysiloxane is a poly(dimethylsiloxane). In an embodiment, the hydrophilic poly(alkylene oxide) is poly(ethylene oxide). In an embodiment, the hydrophobic poly(alylene oxide) is poly(propylene oxide) or poly(tetramethylene oxide). In an embodiment, the endgroup comprises a hydrophobic poly(alkylene oxide), a hydrophilic poly(alkylene oxide), a copolymer comprising a hydrophilic poly(alkylene oxide) and a hydrophobic poly(alkylene oxide), $C_2$-$C_{20}$ alkyl, $C_2$-$C_{16}$ fluoroalkyl, $C_2$-$C_{16}$ fluoroalkyl ether, or copolymers thereof. Such endgroups may be formed with monofunctional alcohols, including carbinols, or amines of the foregoing.

In an embodiment, the endgroup comprises $C_2$-$C_{16}$ fluoroalkyl or $C_2$-$C_{16}$ fluoroalkyl ether. Such endgroups may be formed with monofunctional alcohols or amines comprising $C_2$-$C_{16}$ fluoroalkyl or $C_2$-$C_{16}$ fluoroalkyl ether.

In an embodiment, the endgroup is formed from a monofunctional alcohol or amine comprising $C_2$-$C_{16}$ fluoroalkyl or $C_2$-$C_{16}$ fluoroalkyl ether. In an embodiment, the endgroup is formed from 1H,1H-Perfluoro-3,6-dioxaheptan-1-ol, 1H,1H-Nonafluoro-1-pentanol, 1H,1H-Perfluoro-1-hexyl alcohol, 1H,1H-Perfluoro-3,6,9-trioxadecan-1-ol, 1H,1H-Perfluoro-1-heptyl alcohol, 1H,1H-Perfluoro-3,6-dioxadecan-1-ol, 1H,1H-Perfluoro-1-octyl alcohol, 1H,1H-Perfluoro-1-nonyl alcohol, 1H,1H-Perfluoro-3,6,9-trioxatridecan-1-ol, 1H,1H-Perfluoro-1-decyl alcohol, 1H,1H-Perfluoro-1-undecyl alcohol, 1H,1H-Perfluoro-1-lauryl alcohol, 1H,1H-Perfluoro-1-myristyl alcohol, or 1H,1H-Perfluoro-1-palmityl alcohol.

In an embodiment, the endgroup is monomeric and has a molecular weight of 200 g/mol or more, 300 g/mol or more, or 500 g/mol or more. In an embodiment, the endgroup is monomeric and has a molecular weight of 1,000 g/mol or less or 800 g/mol or less. In an embodiment, the endgroup is polymeric and has a Mn of 10,000 g/mol or less, 8,000 g/mol or less, 6,000 g/mol or less, or 4,000 g/mol or less. In an embodiment, the endgroup is polymeric and has a Mn of 500 g/mol or more, 1,000 g/mol or more, or 2,000 g/mol or more.

In an embodiment, the endgroup is present in an amount of at least 0.1 wt %, at least 0.2 wt %, at least 0.3 wt %, or at least 0.5 wt %, based on the total weight of the formulation from which the polyurethane is formed. In an embodiment, the endgroup is present in an amount of at most 3 wt %, at most 2 wt % or at most 1 wt %, based on the total weight of the formulation from which the polyurethane is formed. In an embodiment, the endgroup is present in an amount of at least 0.1 wt %, at least 0.2 wt %, at least 0.3 wt %, or at least 0.5 wt %, based on the total weight of the polyurethane. In an embodiment, the endgroup is present in an amount of at most 3 wt %, at most 2 wt % or at most 1 wt %, based on the total weight of the polyurethane.

Formation of Polyurethanes

The polyurethanes may be formed as generally known in the art. A catalyst may be employed. In an embodiment, the catalyst is stannous octoate or dibutyltin dilaurate. Amine catalysts may also be used.

Solvent

The compositions also comprise a solvent. To form a membrane, the solvent is evaporated after casting a film from the composition comprising the polyurethane, the free hydrophilic polymer, and the solvent. In an embodiment, the solvent comprises tetrahydrofuran (THF), methyl-tetrahydrofuran (methyl-THF), dimethylacetamide (DMAc), dimethylformamide (DMF), dimethyl sulfoxide (DMSO), or a mixture thereof. In an embodiment, the solvent comprises tetrahydrofuran (THF) or methyl-tetrahydrofuran (methyl-THF).

A co-solvent may also be present. A co-solvent comprises less than 50 wt % of the total amount of solvent. In an embodiment, a co-solvent is present and is methanol, ethanol, isobutanol, propanol, methyl ethyl ketone, or a mixture thereof.

In an embodiment, the solvent comprises 50 wt % or more of tetrahydrofuran (THF), methyl-tetrahydrofuran (methyl-THF), or a mixture thereof and less than 50 wt % of methanol, ethanol, isobutanol, methyl ethyl ketone, or a mixture thereof. In an embodiment, the solvent comprises 40 wt % or more of tetrahydrofuran (THF), methyl-tetrahydrofuran (methyl-THF), or a mixture thereof, and methanol, ethanol, isobutanol, propanol, methyl ethyl ketone, or a mixture thereof at an amount of from 1 to 60 wt %, based on the total amount of solvent in the composition.

In an embodiment, the solvent is present in an amount of from 80 to 99.8 wt % of the composition, from 85 wt % to 99.5 wt %, or from 90 wt % to 99 wt %. In an embodiment, the co-solvent is present at less than 50 wt % of the total amount of solvent, less than 40 wt %, less than 30 wt %, less than 20 wt %, or less than 10 wt %. In an embodiment, the solvent comprises at least 40 wt % of THF, methyl-THF, or a mixture thereof, and methanol, ethanol, or a mixture thereof at an amount of from 1 to 60 wt %, based on the total amount of solvent in the composition. In an embodiment, the solvent comprises at least 40 wt % of THF, and methanol, ethanol, or a mixture thereof at an amount of from 1 to 60 wt %, based on the total amount of solvent in the composition. In an embodiment, the solvent comprises at least 70 wt % of THF, and propanol, isobutanol, methyl-THF, or methyl ethyl ketone, or a mixture thereof, at an amount of from 1 to 30 wt %, based on the total amount of solvent in the composition.

Membranes

Membranes are typically formed by casting the composition comprising the polyurethane, the free hydrophilic polymer, and the solvent directly onto a substrate, such as a sensor, or onto a support liner. The solvent is then evaporated, optionally by use of vacuum or elevated temperatures. Typical temperatures are from 40 to 90° C. Additives, such as a mold release agent, may be present to facilitate the casting process. In an embodiment, the composition further comprises a mold release agent.

In an embodiment, the membrane comprises from 85 to 99.5 wt %, based on the total weight of the membrane, of the polyurethane, and from 0.5 to 15 wt %, based on the total weight of the membrane, of the free hydrophilic polymer.

In an embodiment, a membrane is permeable to both glucose and oxygen. In an embodiment, the membrane or a membrane formed from the composition has a glucose transmission rate of from $1 \times 10^{-10}$ to $9 \times 10^{-9}$ cm$^2$/sec. In an embodiment, the membrane or a membrane formed from the composition has an oxygen transmission rate of from $1 \times 10^{-7}$ to $1 \times 10^{-2}$ cm$^2$/sec. In an embodiment, the membrane or a membrane formed from the composition has an oxygen transmission rate of from $1 \times 10^{-5}$ to $1 \times 10^{-3}$ cm$^2$/sec. In an embodiment, the membrane has a thickness of from 1 to 100 μm.

In an embodiment, the membrane has a residual solvent content of less than 50 ppm after drying the membrane under nitrogen for 24 hours followed by drying in a convection oven at 50° C. for one hour.

Applications

The disclosed membranes find utility in medical devices and sensors. Such sensors may detect a wide range of analytes, including glucose, lactic acid, galactose, alcohol, medicinal or recreational drugs, cholesterol, antigens, antibodies, viruses, vitamins, minerals, nutrients, proteins, amino acids, hormones or neurotransmitters. In an embodiment, a sensor for measuring glucose, lactic acid, glutamate, pyruvate, choline, acetylcholine, nitric oxide, sodium, potassium, calcium, chloride, bicarbonate, urea, creatine, or dopamine in the blood stream or another bodily fluid comprises a membrane as disclosed.

In an embodiment, the membrane comprises an enzyme that is reactive with an analyte. In an embodiment, a sensor comprises the membrane and a second membrane, the second membrane comprising an enzyme that is reactive with an analyte.

The medical devices or sensors may be implantable in the body. In an embodiment, a continuous analyte monitoring system comprises the membrane. In an embodiment, a continuous glucose monitoring system comprises the membrane.

The Examples below further elucidate embodiments of the invention, but of course, should not be construed as in any way limiting the scope of the claims.

EXAMPLES

A polyurethane comprising a silicone and hydrophobic polyether backbone (Sil-PE), a polyurethane comprising a silicone and hydrophobic polyether backbone with fluoroalkyl endgroups (Sil-PE-F), and a polyurethane comprising a polysiloxane and polycarbonate backbone are formed (Sil-PC). The polyurethanes are formed from the stated formulations with the aid of a catalyst and a mold release agent. An antioxidant may also be used. The compositions of these thermoplastic polyurethane materials used in the Examples are shown in Table 0.1. All amounts are shown in weight percent.

TABLE 0.1

Polyurethane Materials

| PU Name | Aromatic Diisocyanate | Hydrophobic polyether diol | Silicone Diol | Polycarbonate Diol | Chain Extender | Silicone mono-ol (Mw ~3,000) | 1H,1H,2H,2H-Perfluoro-1-decanol |
|---|---|---|---|---|---|---|---|
| Sil-PE | 30-40 | 20-30 | 30-40 | | 5-10 | 0.1-1 | |
| Sil-PE-F | 30-40 | 20-30 | 30-40 | | 5-10 | | 0.5-1.5 |
| Sil-PC | 25-35 | | 15-25 | 40-50 | 5-10 | 0.1-1 | |

Solution Viscosity, oxygen permeability, glucose diffusivity, and lactase diffusivity are measured as follows.

Solution Viscosity

Solution viscosity is measured using a calibrated coaxial cylinder viscometer. The spindle and sample cup are held at a constant temperature of 23° C. using an external circulator. Sample is added to the cup and held for at least 30 minutes for temperature equilibration. The sample is then subjected to at least three different shear rates by changing the rotation speed of the spindle. Viscosities are recorded after displacing all bubbles in the solution and after the readings have stabilized. A plastic cap is placed over the sample cup to minimize solvent evaporation during the test.

Oxygen Permeability

Film samples are cut to the appropriate size and masked with foil to seal any leaks. The film thickness is measured. The film is mounted onto a Mocon OxTran 2/20 system and allowed to equilibrate to a constant gas transmission rate, utilizing compressed air as the test gas and 99% nitrogen with 1% hydrogen as the carrier gas. The humidity is 95%. The equilibrium gas transmission rate is recorded and the gas permeability in Barrer is calculated.

Glucose and Lactate Diffusivity

A film of the sample is cut in the shape of a circle (diameter ~6 cm) to remove any curled edges or air bubbles. The thickness of the film is measured 10 times using a thickness gauge. The average of the 10 measurements is used as the film thickness. The film is then mounted between two silicone gaskets with vacuum grease. The inner diameter of the gaskets is ~5 cm. The gaskets are then mounted on a Franz cell apparatus with the receptor cavity filled with deionized water and a magnetic stir bar. The receptor vessel is equipped with sampling ports, in which samples can be removed over time. A top is placed on the receptor vessel which seals the film onto the Franz cell and creates the donor vessel. A concentrated glucose solution (2000 mg/dL) or lactate solution (200 mg/mL) is inserted into the donor vessel. The Franz cell is then closed with a lid to prevent evaporation. 100 microliter samples are taken over a period of 6 hours, under stirring at 800 RPM. Deionized water is used to replace the liquid in the donor vessel and maintain sink conditions.

The liquid samples are then analyzed for glucose content using a glucose colorimetric assay and a UV plate reader. The amount of glucose in each sample is determined using a calibration curve. The slope of mg glucose/cm$^2$ over time is determined. This flux value is then utilized to calculate the diffusivity of the glucose of each film. All films are analyzed in at least duplicate to ensure no leaks are present.

Example 1

Films are formed by casting a composition comprising the stated polyurethane and the stated free hydrophilic polymer in the stated solvent at the stated percent solids. PVP is polyvinylpyrrolidone, PDX is poly(2-ethyl-2-oxazoline), and PEG is poly(ethylene glycol). All films are dried under nitrogen for one hour, followed by drying in an oven at 50° C. for one hour for samples where THF is the listed solvent and at 80° C. for one hour where DMaC is the listed solvent. The films are measured for oxygen permeability and glucose diffusivity in accordance with the above procedure. The results are shown in Table 1, below. The wt % percent of free hydrophilic polymer is based on the total combined weight of polyurethane and free hydrophilic polymer. The percent solids is the percent by weight of free hydrophilic polymer and polyurethane combined in the composition. Any blank values were not measured.

TABLE 1

Example 1 Composition and Results

| Ex. | PU | Free Hydrophilic Polymer | Mw of Hydrophilic Polymer (g/mol) | wt % Free hydrophilic polymer | Solvent | % Solids by weight | Viscosity (cPs) | Oxygen Permeability (Dk) | Glucose Diffusivity (cm$^2$/s) | Lactate Diffusivity (cm$^2$/s) |
|---|---|---|---|---|---|---|---|---|---|---|
| 1 | Sil-PE | POX | 500k | 5 | DMaC | 4.30 | 51.7 | | | |
| 2 | Sil-PE | POX | 500k | 15 | DMaC | 4.78 | 60.3 | | | |
| 3 | Sil-PE | POX | 500k | 35 | DMaC | 6.16 | 85.5 | | | |
| 4 | Sil-PE | PVP | 1000k | 5 | DMaC | 4.36 | 49.8 | 27.6 | $2.85 \times 10^{-11}$ | |
| 5 | Sil-PE | PVP | 1000k | 15 | DMaC | 4.83 | 55.1 | 12.8 | $3.29 \times 10^{-11}$ | |
| 6 | Sil-PE | PVP | 1000k | 35 | DMaC | 6.18 | 58.1 | 26.8 | $2.21 \times 10^{-8}$ | |
| 7 | Sil-PE | PEG | 300k | 5 | DMaC | 4.98 | 105.33 | 21 | $6.63 \times 10^{-10}$ | |
| 8 | Sil-PE | PEG | 300k | 15 | DMaC | 5.01 | 75.42 | 20.4 | $4.98 \times 10^{-10}$ | |
| 9 | Sil-PE | PEG | 300k | 35 | DMaC | 4.99 | 84.42 | | $2.01 \times 10^{-8}$ | |
| 10 | Sil-PE-F | POX | 500k | 1 | THF | 8.7 | 167 | 66 | $<1.0 \times 10^{-12}$ | |
| 11 | Sil-PE-F | POX | 500k | 5 | THF | 8.7 | 214 | 51.5 | $3.13 \times 10^{-11}$ | |
| 12 | Sil-PE-F | PVP | 1000k | 0.25 | THF[1] | 6.35 | 6,620 | | $<1.0 \times 10^{-12}$ | |
| 13 | Sil-PE-F | PVP | 1000k | 0.5 | THF[2] | 6.44 | 5,520 | 27.3 | $<1.0 \times 10^{-12}$ | |
| 14 | Sil-PE-F | POX | 500k | 10 | THF | 9.77 | 292.5 | 27.6 | $9.41 \times 10^{-12}$ | 1.41E-10 |
| 15 | Sil-PE-F | POX | 500k | 20 | THF | 10.86 | 568 | 31.1 | $2.21 \times 10^{-11}$ | 7.53E-11 |

TABLE 1-continued

Example 1 Composition and Results

| Ex. | PU | Free Hydrophilic Polymer | Mw of Hydrophilic Polymer (g/mol) | wt % Free hydrophilic polymer | Solvent | % Solids by weight | Viscosity (cPs) | Oxygen Permeability (Dk) | Glucose Diffusivity (cm$^2$/s) | Lactate Diffusivity (cm$^2$/s) |
|---|---|---|---|---|---|---|---|---|---|---|
| 16 | Sil-PE-F | POX | 500k | 35 | THF | 13.04 | 1266 | | $2.17 \times 10^{-8}$ | 7.47E−11 |
| 17 | Sil-PE-F | PEG | 300k | 5 | THF | 5.01 | 32.47 | 48 | $2.11 \times 10^{-11}$ | |
| 18 | Sil-PE-F | PEG | 300k | 15 | THF | 5.0 | 39.68 | 44.6 | $6.68 \times 10^{-9}$ | |
| 19 | Sil-PE-F | PEG | 300k | 35 | THF | 4.71 | 68.55 | 37.8 | $1.36 \times 10^{-07}$ | |
| 20 | Sil-PE-F | PEG | 300k | 5 | DMaC | 4.99 | 19.88 | | $1.35 \times 10^{-11}$ | |
| 21 | Sil-PE-F | PEG | 300k | 15 | DMaC | 4.97 | 27.41 | | $5.49 \times 10^{-9}$ | |
| 22 | Sil-PE-F | PEG | 300k | 35 | DMaC | 5.01 | | | $1.07 \times 10^{-8}$ | |
| 23 | Sil-PC | POX | 500k | 5 | THF | 8.8 | 499.4 | 8.8 | $5.77 \times 10^{-11}$ | |
| 24 | Sil-PC | POX | 500k | 15 | THF | 4.7 | 871.7 | 4.7 | $6.75 \times 10^{-11}$ | |
| 25 | Sil-PC | POX | 500k | 35 | THF | 4.3 | 2079.7 | 4.3 | $3.40 \times 10^{-7}$ | |
| 26 | Sil-PC | POX | 500k | 5 | DMaC | 8.2 | 340.7 | 8.2 | $1.08 \times 10^{-11}$ | |
| 27 | Sil-PC | POX | 500k | 15 | DMaC | 7.7 | 427.1 | 7.7 | $1.89 \times 10^{-11}$ | |
| 28 | Sil-PC | POX | 500k | 35 | DMaC | 4.7 | 745.7 | 4.7 | $1.27 \times 10^{-8}$ | |
| 29 | Sil-PC | PVP | 1000k | 5 | DMaC | 7.5 | 24.2 | 7.5 | $5.12 \times 10^{-9}$ | |
| 30 | Sil-PC | PVP | 1000k | 15 | DMaC | 7.9 | 35.0 | 7.9 | $6.66 \times 10^{-9}$ | |
| 31 | Sil-PC | PVP | 1000k | 35 | DMaC | 7.7 | 78.8 | 7.7 | $2.59 \times 10^{-8}$ | |
| 32 | Sil-PC | PVP | 1000k | 5 | THF | 3.92 | 17.1 | 4.7 | $1.35 \times 10^{-11}$ | |
| 33 | Sil-PC | PVP | 1000k | 15 | THF | 3.74 | 24.1 | 5.3 | $5.93 \times 10^{-11}$ | |
| 34 | Sil-PC | PVP | 1000k | 35 | THF | 3.73 | 35.6 | 4.7 | $9.13 \times 10^{-9}$ | |

The membranes show selectivity for glucose and, where tested, also lactic acid. The data shows that the membranes comprising PDX as the free hydrophilic polymer may help reduce sensor interference from other small molecules in the body, such as acetaminophen, lowering the limit of detection of the sensor, and extending its lifetime. Membranes made with Sil-PC and PDX show equivalent film performance for glucose diffusivity and oxygen permeability when cast in either THF or DMAc. Compositions made with Sil-PE-F, and THF (Experiments 14-16) show improved viscosity at higher solid content than compositions made with Sil-PE-F, PVP, and THF (Experiments 12-13), and a co-solvent (methanol) is required to dissolve the PVP.

[1] the solvent was 91.4 wt % THF and 2.3 wt % methanol, based on the total weight of the formulation.
[2] the solvent was 89.1 wt % THF and 4.5 wt % methanol, based on the total weight of the formulation.

Membranes formed with PEG are white in appearance when exposed to water or humidified air. The films show poor structural integrity and curl at the edges. The membranes break readily.

Example 2

Various membranes are formed in order to test the effect of a co-solvent on membrane properties from membranes comprising poly(2-ethyl-2-oxazoline) with an Mw of 500,000 g/mol (PDX) as the free hydrophilic polymer. The polyurethane is SIL-PE-F. The films are dried under nitrogen for 24 hours, followed by drying in a convection over at 50° C. for one hour. The films are measured for oxygen permeability and glucose diffusivity in accordance with the above procedure. The wt % shown is based on the composition comprising polyurethane, free hydrophilic polymer, solvent, and co-solvent. Any blank values are not measured. The results are shown in Table 2.

TABLE 2

Example 2 Compositions and Results

| Ex. | PU (wt %) | POX (wt %) | THF (wt %) | Co-Solvent (wt %) | Equilibrium Water Content % | Glucose Diffusivity (cm$^2$/sec) | Oxygen Permeability (Dk) |
|---|---|---|---|---|---|---|---|
| 35 | 9.27 | 1.03 | 89.7 | NA | 4.54% | $9.41 \times 10^{-12}$ | 15.2 |
| 36 | 9.16 | 2.29 | 88.55 | NA | 12.45% | $2.21 \times 10^{-11}$ | 17.9 |
| 37 | 8.92 | 4.8 | 86.28 | NA | 31.76% | $2.17 \times 10^{-8}$ | 12.5 |
| 38 | 3.74 | 2.01 | 42.41 | EtOH 51.84 | 49.62% | $5.43 \times 10^{-8}$ | |
| 40 | 4.19 | 0.74 | 47.54 | EtOH 47.54 | 14.27% | $7.92 \times 10^{-11}$ | |
| 41 | 4.16 | 1.39 | 47.23 | EtOH 47.23 | 21.18% | $8.96 \times 10^{-10}$ | |
| 42 | 3.24 | 1.75 | 90.26 | Propanol 4.75 | 57.44 | $7.14 \times 10^{-10}$ | 10.7 |
| 43 | 3.25 | 1.75 | 85.5 | Propanol 9.5 | 57.63 | $4.12 \times 10^{-10}$ | |
| 44 | 3.25 | 1.75 | 90.3 | Me-THF 4.7 | 45.33 | $1.06 \times 10^{-9}$ | |
| 45 | 3.22 | 1.71 | 85.53 | Me-THF 9.53 | 41.77 | $1.18 \times 10^{-9}$ | |

Additional Description of Exemplary Embodiments

1. A membrane comprising:
   a. a free hydrophilic polymer comprising a polyoxazoline, and
   b. a polyurethane, the polyurethane comprising a backbone comprising the reaction product of a diisocyanate, a polymeric aliphatic diol, and optionally a chain extender.
2. The membrane according to the preceding exemplary embodiment, wherein the membrane comprises from 60 to 99.5 wt %, based on the total weight of the membrane, of the polyurethane, and from 0.5 to 40 wt %, based on the total weight of the membrane, of the free hydrophilic polymer.
3. The membrane according to the preceding exemplary embodiment, wherein the membrane comprises from 70 to 99.5 wt %, based on the total weight of the membrane, of the polyurethane, and from 0.5 to 30 wt %, based on the total weight of the membrane, of the free hydrophilic polymer.
4. The membrane according to the preceding exemplary embodiment, wherein the membrane comprises from 80 to 99.5 wt %, based on the total weight of the membrane, of the polyurethane, and from 0.5 to 20 wt %, based on the total weight of the membrane, of the free hydrophilic polymer.
5. The membrane according to the preceding exemplary embodiment, wherein the membrane comprises from 85 to 99.5 wt %, based on the total weight of the membrane, of the polyurethane, and from 0.5 to 15 wt %, based on the total weight of the membrane, of the free hydrophilic polymer.
6. The membrane according to the preceding exemplary embodiment, wherein the membrane comprises from 90 to 99.5 wt %, based on the total weight of the membrane, of the polyurethane, and from 0.5 to 10 wt %, based on the total weight of the membrane, of the free hydrophilic polymer.
7. The membrane according to the preceding exemplary embodiment, wherein the membrane comprises from 60 to 99 wt %, based on the total weight of the membrane, of the polyurethane, and from 1.0 to 40 wt %, based on the total weight of the membrane, of the free hydrophilic polymer.
8. The membrane according to the preceding exemplary embodiment, wherein the membrane comprises from 70 to 99 wt %, based on the total weight of the membrane, of the polyurethane, and from 1.0 to 30 wt %, based on the total weight of the membrane, of the free hydrophilic polymer.
9. The membrane according to the preceding exemplary embodiment, wherein the membrane comprises from 80 to 99 wt %, based on the total weight of the membrane, of the polyurethane, and from 1.0 to 20 wt %, based on the total weight of the membrane, of the free hydrophilic polymer.
10. The membrane according to the preceding exemplary embodiment, wherein the membrane comprises from 85 to 99 wt %, based on the total weight of the membrane, of the polyurethane, and from 1.0 to 15 wt %, based on the total weight of the membrane, of the free hydrophilic polymer.
11. The membrane according to the preceding exemplary embodiment, wherein the membrane comprises from 90 to 99 wt %, based on the total weight of the membrane, of the polyurethane, and from 1.0 to 10 wt %, based on the total weight of the membrane, of the free hydrophilic polymer.
12. A composition for forming a membrane comprising from 90 to 99.5 wt %, based on the total weight of the composition, of a solvent and from 0.5 to 10 wt %, based on the total weight of the composition, of a polymer mixture, the polymer mixture comprising from 60 to 99.5 wt %, based on the total weight of the polymer mixture, of a polyurethane and from 0.5 to 40 wt %, based on the total weight of the polymer mixture, of a free hydrophilic polymer comprising a polyoxazoline,
wherein the polyurethane comprises a backbone comprising the reaction product of a diisocyanate, a polymeric aliphatic diol, and optionally a chain extender.
13. The composition according to the preceding exemplary embodiment, wherein the polymer mixture comprises from 70 to 99.5 wt %, based on the total weight of the membrane, of the polyurethane, and from 0.5 to 30 wt %, based on the total weight of the membrane, of the free hydrophilic polymer.
14. The composition according to the preceding exemplary embodiment, wherein the polymer mixture comprises from 80 to 99.5 wt %, based on the total weight of the membrane, of the polyurethane, and from 0.5 to 20 wt %, based on the total weight of the membrane, of the free hydrophilic polymer.
15. The composition according to the preceding exemplary embodiment, wherein the polymer mixture comprises from 85 to 99.5 wt %, based on the total weight of the membrane, of the polyurethane, and from 0.5 to 15 wt %, based on the total weight of the membrane, of the free hydrophilic polymer.
16. The composition according to the preceding exemplary embodiment, wherein the polymer mixture comprises from 85 to 99.5 wt %, based on the total weight of the membrane, of the polyurethane, and from 0.5 to 15 wt %, based on the total weight of the membrane, of the free hydrophilic polymer.
17. The composition according to the preceding exemplary embodiment, wherein the polymer mixture comprises from 90 to 99.5 wt %, based on the total weight of the membrane, of the polyurethane, and from 0.5 to 10 wt %, based on the total weight of the membrane, of the free hydrophilic polymer.
18. The composition or membrane according to any one of the preceding exemplary embodiments, wherein the free hydrophilic polymer consists of a polyoxazoline.
19. The composition or membrane according to any one of the preceding exemplary embodiments, wherein the free hydrophilic polymer comprises a poly(2-methyl-2-oxazoline) or a poly(2-ethyl-2-oxazoline).
20. The composition or membrane according to any one of the preceding exemplary embodiments, wherein free hydrophilic polymer consists of a poly(2-methyl-2-oxazoline), a poly(2-ethyl-2-oxazoline), a mixture thereof, or a copolymer thereof.
21. The composition or membrane according to any one of the preceding exemplary embodiments, wherein the free hydrophilic polymer comprises a polyoxazoline and one or more of a poly(ethylene oxide), polyvinylpyrrolidone, polyacrylic acid, polyvinyl alcohol, or hyaluronic acid.
22. The composition or membrane according to any one of the preceding exemplary embodiments, wherein the free hydrophilic polymer comprises a polyoxazoline and a polyvinylpyrrolidone.

23. The composition or membrane according to any one of the preceding exemplary embodiments, wherein the free hydrophilic polymer has a number average molecular weight of at least 5,000 g/mol, at least 10,000 g/mol, at least 50,000 g/mol, at least 100,000 g/mol, or at least 200,000 g/mol.

24. The composition or membrane according to any one of the preceding exemplary embodiments, wherein the free hydrophilic polymer has a number average molecular weight of at most 10,000,000 g/mol, at most 5,000,000 g/mol, at most 2,000,000 g/mol, at most 1,000,000 g/mol, at most 500,000 g/mol, or at most 200,000 g/mol.

25. The composition or membrane according to any one of the preceding exemplary embodiments, wherein the polyurethane comprises a $C_2$-$C_{16}$ fluoroalkyl or $C_2$-$C_{16}$ fluoroalkyl ether.

26. The membrane or composition according to any one of the preceding exemplary embodiments, wherein the backbone comprises a $C_2$-$C_{16}$ fluoroalkyl or $C_2$-$C_{16}$ fluoroalkyl ether.

27. The membrane or composition according to any one of the preceding exemplary embodiments, wherein the polyurethane comprises an endgroup that comprises a $C_2$-$C_{16}$ fluoroalkyl or $C_2$-$C_{16}$ fluoroalkyl ether.

28. The membrane or composition according to any one of the preceding exemplary embodiments, wherein both the backbone and an endgroup of the polyurethane comprise a $C_2$-$C_{16}$ fluoroalkyl or $C_2$-$C_{16}$ fluoroalkyl ether.

29. The membrane or composition according to any one of the preceding exemplary embodiments, wherein the polyurethane comprises at least 1 wt %, at least 2 wt %, or at least 5 wt % of $C_2$-$C_{16}$ fluoroalkyl or $C_2$-$C_{16}$ fluoroalkyl ether, based on the total weight of the polyurethane.

30. The membrane or composition according to any one of the preceding exemplary embodiments, wherein the polyurethane comprises at most 15 wt %, at most 10 wt %, or at most 8 wt % of $C_2$-$C_{16}$ fluoroalkyl or $C_2$-$C_{16}$ fluoroalkyl ether, based on the total weight of the polyurethane.

31. The composition or membrane according to any one of the preceding exemplary embodiments, wherein the polyurethane comprises a polysiloxane.

32. The membrane or composition according to any one of the preceding exemplary embodiments, wherein the backbone comprises a polysiloxane.

33. The membrane or composition according to any one of the preceding exemplary embodiments, wherein the polyurethane comprises an endgroup that comprises a polysiloxane.

34. The membrane or composition according to any one of the preceding exemplary embodiments, wherein both the backbone and an endgroup of the polyurethane comprise a polysiloxane.

35. The membrane or composition according to any one of the preceding exemplary embodiments, wherein the polyurethane comprises at least 5 wt %, at least 10 wt %, or at least 15 wt % of polysiloxane, based on the total weight of the polyurethane.

36. The membrane or composition according to any one of the preceding exemplary embodiments, wherein the polyurethane comprises at most 50 wt %, at most 40 wt %, or at most 30 wt % of polysiloxane, based on the total weight of the polyurethane 37. The membrane or composition according to any one of the preceding exemplary embodiments, wherein the polyurethane is substantially devoid of or devoid of endgroups comprising polysiloxane moieties.

38. The membrane or composition according to any one of the preceding exemplary embodiments, wherein the membrane or composition is devoid of siloxane.

39. The membrane or composition according to any one of the preceding exemplary embodiments, wherein the polyurethane is devoid of siloxane.

40. The membrane or composition according to any one of the preceding exemplary embodiments, wherein the polyurethane is a thermoplastic polyurethane.

41. The membrane or composition according to any one of the preceding exemplary embodiments, wherein the polyurethane is linear.

42. The membrane or composition according to any one of the preceding exemplary embodiments, wherein the polyurethane is devoid of a hydrophilic polymer moiety.

43. The membrane or composition according to any one of the preceding exemplary embodiments, wherein the polyurethane is devoid of polyethylene oxide and polyoxazoline.

44. The membrane or composition according to any one of the preceding exemplary embodiments, wherein the polyurethane is devoid of polyethylene oxide.

45. The membrane or composition according to any one of the preceding exemplary embodiments, wherein the polyurethane backbone comprises the residue of a fluoroalkyl or fluoroalkyl ether diol.

46. The membrane or composition according to any one of the preceding exemplary embodiments, wherein the polyurethane backbone comprises the residue of a fluoroalkyl or fluoroalkyl ether diol or diamine.

47. The membrane or composition according to any one of the preceding exemplary embodiments, wherein the polyurethane backbone comprises the residue of 1H,1H,4H,4H-Perfluoro-1,4-butanediol, 1H,1H,5H,5H-Perfluoro-1,5-pentanediol, 1H,1H,6H,6H-perfluoro-1,6-hexanediol, 1H,1H,8H,8H-Perfluoro-1,8-octanediol, 1H,1H,9H,9H-Perfluoro-1,9-nonanediol, 1H,1H,10H,10H-Perfluoro-1,10-decanediol, 1H,1H,12H,12H-Perfluoro-1,12-dodecanediol, 1H,1H,8H,8H-Perfluoro-3,6-dioxaoctan-1,8-diol, 1H,1H,11H,11H-Perfluoro-3,6,9-trioxaundecan-1,11-diol. fluorinated triethylene glycol, or fluorinated tetraethylene glycol.

48. The membrane or composition according to any one of the preceding exemplary embodiments, wherein the polyurethane backbone comprises a block comprising fluoroalkyl or fluoroalkyl ether having an Mn of at least 150 g/mol, at least 250 g/mol, or at least 500 g/mol.

49. The membrane or composition according to any one of the preceding exemplary embodiments, wherein the prepolymer comprises a block comprising fluoroalkyl or fluoroalkyl ether having a Mn of at most 1500 g/mol, at most 1000 g/mol, or at most 850 g/mol.

50. The membrane or composition according to any one of the preceding exemplary embodiments, wherein the backbone of the polyurethane comprises at least 1 wt %, at least 2 wt %, or at least 5 wt % of $C_2$-$C_{16}$ fluoroalkyl or $C_2$-$C_{16}$ fluoroalkyl ether, based on the total weight of the backbone.

51. The membrane or composition according to any one of the preceding exemplary embodiments, wherein the backbone of the polyurethane comprises at most 15 wt %, at most 10 wt %, or at most 8 wt % of $C_2$-$C_{16}$ fluoroalkyl or $C_2$-$C_{16}$ fluoroalkyl ether, based on the total weight of the backbone.

52. The membrane or composition according to any one of the preceding exemplary embodiments, wherein the backbone of the polyurethane consists of the reaction product of:
   i. a diisocyanate;
   ii. a polymeric aliphatic diol; and
   iii. a chain extender.
53. The membrane or composition according to any one of the preceding exemplary embodiments, wherein the backbone of the polyurethane consists of the reaction product of:
   i. a diisocyanate;
   ii. a polymeric aliphatic diol;
   iii. a chain extender; and
   iv. a diol comprising a $C_2$-$C_{16}$ fluoroalkyl or $C_2$-$C_{16}$ fluoroalkyl ether.
54. The membrane or composition according to any one of preceding exemplary embodiments, wherein the diisocyanate is an aliphatic diisocyanate.
55. The membrane or composition according to any one of the preceding exemplary embodiments, wherein the diisocyanate comprises 4,4'-diphenylmethane diisocyanate (MDI), 2,4-toluene diisocyanate, 2,6-toluene diisocyanate, 1,4-phenylene diisocyanate, hexamethylene diisocyanate (HDI), tetramethylene-1,4-diisocyanate, cyclohexane-1,4-diisocyanate, dicyclohexylmethane-4,4'-diisocyanate (HMDI), isophorone diisocyanate (IPDI), or a mixture thereof.
56. The membrane or composition according to any one of the preceding exemplary embodiments, wherein the diisocyanate comprises hexamethylene diisocyanate, dicyclohexylmethane 4,4'-diisocyanate, isophorone diisocyanate, or a mixture thereof.
57. The membrane or composition according to any one of the preceding exemplary embodiments, wherein the diisocyanate consists of hexamethylene diisocyanate, dicyclohexylmethane 4,4'-diisocyanate, isophorone diisocyanate, or a mixture thereof.
58. The membrane or composition according to any one of preceding exemplary embodiments, wherein the diisocyanate is an aromatic diisocyanate.
59. The membrane or composition according to any one of preceding exemplary embodiments, wherein the diisocyanate comprises 4,4'-diphenylmethane diisocyanate (MDI), 2,4-toluene diisocyanate, 2,6-toluene diisocyanate, or 1,4-phenylene diisocyanate.
60. The membrane or composition according to any one of preceding exemplary embodiments, wherein the diisocyanate consists of 4,4'-diphenylmethane diisocyanate (MDI), 2,4-toluene diisocyanate, 2,6-toluene diisocyanate, 1,4-phenylene diisocyanate, or a mixture thereof.
61. The membrane or composition according to any one of the preceding exemplary embodiments, wherein the diisocyanate comprises an average of from 1.9 to 2.7 isocyanate groups per molecule.
62. The membrane or composition according to any one of the preceding exemplary embodiments, wherein the diisocyanate has a molecular weight of from 100 to 500 g/mol, or from 150 to 260 g/mol.
63. The membrane or composition according to any one of the preceding exemplary embodiments, wherein the formulation from which the polyurethane is formed comprises at least 10 wt %, at least 20 wt %, at least 25 wt %, at least 30 wt %, at least 35 wt %, or at least 40 wt % of a diisocyanate, based on the total weight of the formulation from which the polyurethane is formed.
64. The membrane or composition according to any one of the preceding exemplary embodiments, wherein the polyurethane is formed from a formulation that comprises at most 50 wt %, at most 40 wt %, at most 35 wt %, at most 30 wt %, at most 25 wt %, or at most 20 wt % of a diisocyanate, based on the total weight of the formulation.
65. The membrane or composition according to any one of the preceding exemplary embodiments, wherein the polyurethane comprises at least 10 wt %, at least 20 wt %, at least 25 wt %, at least 30 wt %, at least 35 wt %, or at least 40 wt % of the residue of a diisocyanate, based on the total weight of the polyurethane.
66. The membrane or composition according to any one of the preceding exemplary embodiments, wherein the polyurethane comprises at most 50 wt %, at most 40 wt %, at most 35 wt %, at most 30 wt %, at most 25 wt %, or at most 20 wt % of the residue of a diisocyanate, based on the total weight of the polyurethane.
67. The membrane or composition according to any one of the preceding exemplary embodiments, wherein the polymeric aliphatic diol comprises $C_2$-$C_{16}$ fluoroalkyl or $C_2$-$C_{16}$ fluoroalkyl ether.
68. The membrane or composition according to any one of the preceding exemplary embodiments, wherein the polymeric aliphatic diol comprises a poly(alkylene oxide), a polycarbonate, a polysiloxane, a random or block copolymer thereof, or a mixture thereof.
69. The membrane or composition according to any one of the preceding exemplary embodiments, wherein the polymeric aliphatic diol comprises a poly(alkylene oxide), a polycarbonate, a random or block copolymer thereof, or a mixture thereof.
70. The membrane or composition according to any one of the preceding exemplary embodiments, wherein the polymeric aliphatic diol comprises a poly(ethylene oxide) diol, a poly(propylene oxide) diol, a poly(tetramethylene oxide) diol, a poly(isobutylene) diol, a poly(hexamethylene carbonate) diol, a poly(polytetrahydrofuran carbonate) diol, a polysiloxane diol, a random or block copolymer diol of poly(ethylene oxide) and poly(propylene oxide), a random or block copolymer diol of poly(ethylene oxide) and poly(tetramethylene oxide), a random or block copolymer diol of poly(ethylene oxide) and a polysiloxane, or a mixture thereof.
71. The membrane or composition according to any one of the preceding exemplary embodiments, wherein the polymeric aliphatic diol comprises a polycarbonate diol that comprises a poly(hexamethylene carbonate) diol or a poly(polytetrahydrofuran carbonate) diol.
72. The membrane or composition according to any one of the preceding exemplary embodiments, wherein the polymeric aliphatic diol comprises a polycarbonate diol.
73. The membrane or composition according to any one of the preceding exemplary embodiments, wherein the polymeric aliphatic diol consists of a polycarbonate diol.
74. The membrane or composition according to any one of the preceding exemplary embodiments, wherein the polymeric aliphatic diol consists of a poly(hexamethylene carbonate) diol, a poly(polytetrahydrofuran carbonate) diol, or a mixture thereof.
75. The membrane or composition according to any one of the preceding exemplary embodiments, wherein the polymeric aliphatic diol comprises a polysiloxane diol or a random or block copolymer diol comprising a polysiloxane.
76. The membrane or composition according to any one of the preceding exemplary embodiments, wherein the polymeric aliphatic diol comprises a polycarbonate diol having a Mn of at least 500 g/mol, at least 750 g/mol, at least 1000 g/mol, or at least 1500 g/mol.

77. The membrane or composition according to any one of the preceding exemplary embodiments, wherein the polymeric aliphatic diol comprises a polycarbonate diol having a Mn of at most 10,000 g/mol, at most 7500 g/mol, at most 5000 g/mol, at most 4000 g/mol, at most 3000 g/mol, or at most 2500 g/mol.

78. The membrane or composition according to any one of the preceding exemplary embodiments, wherein the polymeric aliphatic diol has a Mn of at least 200 g/mol, at least 250 g/mol, at least 300 g/mol, at least 400 g/mol, or at least 500 g/mol, at least 600 g/mol, at least 700 g/mol, at least 800 g/mol, at least 900 g/mol, or at least 1000 g/mol.

79. The membrane or composition according to any one of the preceding exemplary embodiments, wherein the polymeric aliphatic diol has a Mn of at most 10,000 g/mol, at most 8500 g/mol, at most 6000 g/mol, at most 5000 g/mol, at most 4000 g/mol, at most 3000 g/mol, at most 2000 g/mol, or at most 1500 g/mol.

80. The membrane or composition according to any one of the preceding exemplary embodiments, wherein the polymeric aliphatic diol comprises 15 wt % or less, 10 wt % or less, 5 wt % or less, 2 wt % or less, based on the total weight of polymeric aliphatic diol, or is devoid of, hydrophobic poly(alkylene oxide) and polysiloxane.

81. The membrane or composition according to any one of the preceding exemplary embodiments, wherein the polymeric aliphatic diol comprises a polysiloxane diol, a polycarbonate diol, or a poly(tetramethylene oxide) diol.

82. The membrane or composition according to any one of the preceding exemplary embodiments, wherein the polymeric aliphatic diol consists of a polysiloxane diol, a polycarbonate diol, a poly(tetramethylene oxide) diol, or a mixture thereof.

83. The membrane or composition according to any one of the preceding exemplary embodiments, wherein the polymeric aliphatic diol comprises a mixture of two or more of a polysiloxane diol, a polycarbonate diol, or a poly(tetramethylene oxide) diol.

84. The membrane or composition according to any one of the preceding exemplary embodiments, wherein the polymeric aliphatic diol consists of a mixture of two or more of a polysiloxane diol, a polycarbonate diol, or a poly(tetramethylene oxide) diol.

85. The membrane or composition according to any one of the preceding exemplary embodiments, wherein the polymeric aliphatic diol comprises a polysiloxane diol and one or more of a polycarbonate diol and a poly(tetramethylene oxide) diol.

86. The membrane or composition according to any one of the preceding exemplary embodiments, wherein the polymeric aliphatic diol consists of a polysiloxane diol and one or more of a polycarbonate diol and a poly(tetramethylene oxide) diol.

87. The membrane or composition according to any one of the preceding exemplary embodiments, wherein the polymeric aliphatic diol is devoid of hydrophilic polymeric aliphatic diol.

88. The membrane or composition according to any one of the preceding exemplary embodiments, wherein the polymeric aliphatic diol is devoid of polyethylene oxide.

89. The membrane or composition according to any one of the preceding exemplary embodiments, wherein the polymeric aliphatic diol comprises 15 wt % or less, 10 wt % or less, 5 wt % or less, 2 wt % or less, based on the total weight of polymeric aliphatic diol, or is devoid of, poly(propylene oxide), and poly(tetramethylene oxide), and polydimethylsiloxane.

90. The membrane or composition according to any one of the preceding exemplary embodiments, wherein the polyurethane is formed from a formulation that comprises at least 20 wt %, at least 30 wt %, at least 40 wt %, at least 50 wt %, or at least 60 wt % of a polymeric aliphatic diol, based on the total weight of the formulation.

91. The membrane or composition according to any one of the preceding exemplary embodiments, wherein the polyurethane is formed from a formulation that comprises at most 80 wt %, at most 70 wt %, at most 60 wt %, or at most 50 wt % of a polymeric aliphatic diol, based on the total weight of the formulation.

92. The membrane or composition according to any one of the preceding exemplary embodiments, wherein the polyurethane comprises at least 20 wt %, at least 30 wt %, at least 40 wt %, at least 50 wt %, or at least 60 wt % of the residue of a polymeric aliphatic diol, based on the total weight of the polyurethane.

93. The membrane or composition according to any one of the preceding exemplary embodiments, wherein the polyurethane comprises at most 80 wt %, at most 70 wt %, at most 60 wt %, or at most 50 wt % of the residue of a polymeric aliphatic diol, based on the total weight of the polyurethane.

94. The membrane or composition according to any one of the preceding exemplary embodiments, wherein the chain extender has a molecular weight of at least 60 g/mol, at least 70 g/mol, at least 80 g/mol, at least 90 g/mol, or at least 100 g/mol.

95. The membrane or composition according to any one of the preceding exemplary embodiments, wherein the chain extender has a molecular weight of at most 500 g/mol, at most from 400 g/mol, at most 300 g/mol, at most 200 g/mol, or at most 150 g/mol.

96. The membrane or composition according to any one of the preceding exemplary embodiments, wherein the chain extender comprises ethylene glycol, diethylene glycol, propylene glycol, dipropylene glycol, 1,3-propanediol, 1,4-butanediol, 1,5-pentanediol, 1,6-hexanediol, or 1,8-octanediol.

97. The membrane or composition according to any one of the preceding exemplary embodiments, wherein the chain extender consists of one or more of ethylene glycol, diethylene glycol, propylene glycol, dipropylene glycol, 1,3-propanediol, 1,4-butanediol, 1,5-pentanediol, 1,6-hexanediol, or 1,8-octanediol.

98. The membrane or composition according to any one of the preceding exemplary embodiments, wherein the polyurethane is formed from a formulation that comprises at least 1 wt %, at least 2 wt %, at least 5 wt %, at least 8 wt %, or at least 10 wt % of a chain extender, based on the total weight of the formulation.

99. The membrane or composition according to any one of the preceding exemplary embodiments, wherein the polyurethane is formed from a formulation that comprises at most 20 wt %, at most 15 wt %, at most 12 wt %, at most 10 wt %, at most 8 wt %, or at most 5 wt %, of a chain extender, based on the total weight of the formulation.

100. The membrane or composition according to any one of the preceding exemplary embodiments, wherein the polyurethane comprises at least 1 wt %, at least 2 wt %, at least 5 wt %, at least 8 wt %, or at least 10 wt % of the residue of a chain extender, based on the total weight of the polyurethane.

101. The membrane or composition according to any one of the preceding exemplary embodiments, wherein the polyurethane comprises at most 20 wt %, at most 15 wt %, at most 12 wt %, at most 10 wt %, at most 8 wt %, or at most 5 wt %, of the residue of a chain extender, based on the total weight of the polyurethane.

102. The membrane or composition according to any one of the preceding exemplary embodiments, wherein the polyurethane comprises an endgroup.

103. The membrane or composition according to any one of the preceding exemplary embodiments, wherein the polyurethane comprises a linear endgroup.

104. The membrane or composition according to any one of the preceding exemplary embodiments, wherein the polyurethane comprises a branched endgroup.

105. The membrane or composition according to any one of the preceding exemplary embodiments, wherein the polyurethane is linear and further comprises an endgroup at each terminus of the backbone.

106. The membrane or composition according to any one of the preceding exemplary embodiments, wherein the polyurethane comprises an average of the polyurethane comprises an average of at least 0.1 endgroups, at least 0.25 endgroups, at least 0.5 endgroups, at least 1 endgroup, at least 1.5 endgroups, at least 1.8 endgroups, about 2 endgroups, or at least 2 endgroups.

107. The membrane or composition according to any one of the preceding exemplary embodiments, wherein the polyurethane comprises an endgroup comprising a $C_2$-$C_{16}$ fluoroalkyl or $C_2$-$C_{16}$ fluoroalkyl ether.

108. The membrane or composition according to any one of the preceding exemplary embodiments, wherein the endgroup is formed from a monofunctional alcohol or amine comprising $C_2$-$C_{16}$ fluoroalkyl or $C_2$-$C_{16}$ fluoroalkyl ether.

109. The membrane or composition according to any one of the preceding exemplary embodiments, wherein the endgroup is formed from 1H,1H-Perfluoro-3,6-dioxaheptan-1-ol, 1H, 1H-Nonafluoro-1-pentanol, 1H,1H-Perfluoro-1-hexyl alcohol, 1H,1H-Perfluoro-3,6,9-trioxadecan-1-ol, 1H,1H-Perfluoro-1-heptyl alcohol, 1H,1H-Perfluoro-3,6-dioxadecan-1-ol, 1H,1H-Perfluoro-1-octyl alcohol, 1H,1H-Perfluoro-1-nonyl alcohol, 1H,1H-Perfluoro-3,6,9-trioxatridecan-1-ol, 1H,1H-Perfluoro-1-decyl alcohol, 1H,1H-Perfluoro-1-undecyl alcohol, 1H,1H-Perfluoro-1-lauryl alcohol, 1H,1H-Perfluoro-1-myristyl alcohol, or 1H,1H-Perfluoro-1-palmityl alcohol.

110. The membrane or composition according to any one of the preceding exemplary embodiments, wherein the endgroup comprises a hydrophobic poly(alkylene oxide), a hydrophilic poly(alkylene oxide), a copolymer comprising a hydrophilic poly(alkylene oxide) and a hydrophobic poly(alkylene oxide), a polysiloxane, $C_2$-$C_{20}$ alkyl, $C_2$-$C_{16}$ fluoroalkyl, $C_2$-$C_{16}$ fluoroalkyl ether, or copolymers thereof.

111. The membrane or composition according to any one of the preceding exemplary embodiments, wherein endgroup comprises a poly(dimethylsiloxane).

112. The membrane or composition according to any one of the preceding exemplary embodiments, wherein endgroup comprises poly(ethylene oxide).

113. The membrane or composition according to any one of the preceding exemplary embodiments, wherein the endgroup comprises poly(propylene oxide) or poly(tetramethylene oxide).

114. The membrane or composition according to any one of the preceding exemplary embodiments, wherein the endgroup comprises a hydrophobic poly(alkylene oxide), a hydrophilic poly(alkylene oxide), a copolymer comprising a hydrophilic poly(alkylene oxide) and a hydrophobic poly(alkylene oxide), $C_2$-$C_{20}$ alkyl, $C_2$-$C_{16}$ fluoroalkyl, $C_2$-$C_{16}$ fluoroalkyl ether, or copolymers thereof.

115. The membrane or composition according to any one of the preceding exemplary embodiments, wherein the endgroup is monomeric and has a molecular weight of 200 g/mol or more, 300 g/mol or more, or 500 g/mol or more.

116. The membrane or composition according to any one of the preceding exemplary embodiments, wherein the endgroup is monomeric and has a molecular weight of 1,000 g/mol or less or 800 g/mol or less.

117. The membrane or composition according to any one of the preceding exemplary embodiments, wherein the endgroup is polymeric and has a Mn of 10,000 g/mol or less, 8,000 g/mol or less, 6,000 g/mol or less, or 4,000 g/mol or less.

118. The membrane or composition according to any one of the preceding exemplary embodiments, wherein the endgroup is polymeric and has a Mn of 500 g/mol or more, 1,000 g/mol or more, or 2,000 g/mol or more.

119. The membrane or composition according to any one of the preceding exemplary embodiments, wherein the endgroup is present in an amount of at least 0.1 wt %, at least 0.2 wt %, at least 0.3 wt %, or at least 0.5 wt %, based on the total weight of the formulation from which the polyurethane is formed.

120. The membrane or composition according to any one of the preceding exemplary embodiments, wherein the endgroup is present in an amount of at most 3 wt %, at most 2 wt % or at most 1 wt %, based on the total weight of the formulation from which the polyurethane is formed.

121. The membrane or composition according to any one of the preceding exemplary embodiments, wherein the endgroup is present in an amount of at least 0.1 wt %, at least 0.2 wt %, at least 0.3 wt %, or at least 0.5 wt %, based on the total weight of the polyurethane.

122. The membrane or composition according to any one of the preceding exemplary embodiments, wherein the endgroup is present in an amount of at most 3 wt %, at most 2 wt % or at most 1 wt %, based on the total weight of the polyurethane.

123. The membrane or composition according to any one of the preceding exemplary embodiments, wherein the polyurethane comprises a backbone or an endgroup comprising $C_2$-$C_{16}$ fluoroalkyl or $C_2$-$C_{16}$ fluoroalkyl ether.

124. The composition according to any one of the preceding exemplary embodiments, wherein the free hydrophilic polymer is present in an amount of at least 1.0 wt %, at least 1.5 wt %, at least 2 wt %, or at least 2.5 wt %, based on the total weight of the composition.

125. The composition according to any one of the preceding exemplary embodiments, wherein the free hydrophilic polymer is present in an amount of at most 6 wt %, at most 5.5 wt %, at most 5 wt %, or at most 4.5 wt %, based on the total weight of the composition.

126. The composition or membrane according to any one of the preceding exemplary embodiments, wherein the free hydrophilic polymer is present in an amount of at least 2.5%, at least 5%, at least 7.5 wt %, at least 10 wt %, at least 15 wt %, at least 20 wt %, or at least 25 wt %, based on the total combined weight of the polyurethane and the free hydrophilic polymer.

127. The composition or membrane according to any one of the preceding exemplary embodiments, wherein the free hydrophilic polymer is present in an amount of at most 50 wt %, at most 45 wt %, at most 40 wt %, at most 35 wt %, at most 30 wt %, or at most 25 wt %, based on the total combined weight of the polyurethane and the free hydrophilic polymer.

128. The composition according to any one of the preceding exemplary embodiments, wherein the solvent comprises tetrahydrofuran (THF), methyl-tetrahydrofuran (methyl-THF), dimethylacetamide (DMAc), dimethylformamide (DMF), or dimethyl sulfoxide (DMSO).

129. The composition according to any one of the preceding exemplary embodiments, wherein the solvent consists of tetrahydrofuran (THF), methyl-tetrahydrofuran (methyl-THF), or a mixture thereof.

130. The composition according to any one of the preceding exemplary embodiments, wherein the solvent comprises tetrahydrofuran (THF), methyl-tetrahydrofuran (methyl-THF), or a mixture thereof and where co-solvent is present and is methanol, ethanol, isobutanol, propanol, methyl ethyl ketone, or a mixture thereof 131. The composition according to any one of the preceding exemplary embodiments, wherein the solvent comprises less than 50 wt %, less than 40 wt %, less than 30 wt %, less than 20 wt %, or less than 10 wt % of methanol, ethanol, isobutanol, propanol, methyl ethyl ketone, or a mixture thereof.

132. The composition according to any one of the preceding exemplary embodiments, wherein the solvent comprises 50 wt % or more of tetrahydrofuran (THF), methyl-tetrahydrofuran (methyl-THF), or a mixture thereof and less than 50 wt % of methanol, ethanol, isobutanol, propanol, methyl ethyl ketone, or a mixture thereof.

133. The composition according to any one of the preceding exemplary embodiments, wherein the solvent comprises 40 wt % or more of tetrahydrofuran (THF), methyl-tetrahydrofuran (methyl-THF), or a mixture thereof, and methanol, ethanol, isobutanol, propanol, methyl ethyl ketone, or a mixture thereof at an amount of from 1 to 60 wt %, based on the total amount of solvent in the composition.

134. The composition according to any one of the preceding exemplary embodiments, wherein the solvent is present in an amount of from 85 wt % to 99.5 wt % or from 90 wt % to 99 wt %, based on the total weight of the composition.

135. The composition according to any one of the preceding exemplary embodiments, wherein the solvent comprises at least 40 wt % of THF, methyl-THF, or a mixture thereof, and methanol, ethanol, or a mixture thereof at an amount of from 1 to 60 wt %, based on the total amount of solvent in the composition.

136. The composition according to any one of the preceding exemplary embodiments, wherein the solvent comprises at least 40 wt % of THF, and methanol, ethanol, or a mixture thereof at an amount of from 1 to 60 wt %, based on the total amount of solvent in the composition.

137. The composition according to any one of the preceding exemplary embodiments, wherein the solvent comprises at least 70 wt % of THF, and propanol, isobutanol, methyl-THF, or methyl ethyl ketone, or a mixture thereof, at an amount of from 1 to 30 wt %, based on the total amount of solvent in the composition.

138. The composition according to any one of the preceding exemplary embodiments, wherein the solvent comprises at least 80 wt % of THF, and propanol, isobutanol, methyl-THF, or methyl ethyl ketone, or a mixture thereof, at an amount of from 1 to 20 wt %, based on the total amount of solvent in the composition.

139. The composition according to any one of the preceding exemplary embodiments, wherein the solvent comprises at least 85 wt % of THF, and propanol, isobutanol, methyl-THF, or methyl ethyl ketone, or a mixture thereof, at an amount of from 1 to 15 wt %, based on the total amount of solvent in the composition.

140. A membrane formed from the composition according to any one of the preceding exemplary embodiments.

141. A method of forming a membrane comprising the steps of:
   a. forming a film from the composition according to any one of the preceding exemplary embodiments, and
   b. evaporating the solvent.

142. A membrane formed according the method of the previous exemplary embodiment.

143. The membrane according to any one of the preceding exemplary embodiments, wherein the membrane has a glucose transmission rate of from $1 \times 10^{-10}$ to $9 \times 10^{-9}$ cm$^2$/sec 144. The membrane according to any one of the preceding exemplary embodiments, wherein the membrane has an oxygen transmission rate of from $1 \times 10^{-7}$ to $1 \times 10^{-2}$ cm$^2$/sec 145. The membrane according to any one of the preceding exemplary embodiments, wherein the membrane has an oxygen transmission rate of from $1 \times 10^{-5}$ to $1 \times 10^{-3}$ cm$^2$/sec.

146. The membrane according to any one of the preceding exemplary embodiments, wherein the membrane has a thickness of from 1 to 100 µm.

147. The membrane according to any one of the preceding exemplary embodiments, wherein the membrane has a residual solvent content of less than 50 ppm after drying the membrane under nitrogen for 24 hours followed by drying in a convection oven at 50° C. for one hour.

148. A sensor comprising the membrane according to any one of the preceding exemplary embodiments.

149. A sensor comprising the membrane according to any one of the preceding exemplary embodiments, wherein the sensor is configured to detect glucose, lactic acid, glutamate, pyruvate, choline, acetylcholine, nitric oxide, sodium, potassium, calcium, chloride, bicarbonate, urea, creatine, or dopamine in the blood stream or another bodily fluid.

150. A medical device comprising the membrane according to any one of the preceding exemplary embodiments.

151. A continuous analyte monitoring system comprising the membrane according to any one of the preceding exemplary embodiments.

152. A continuous glucose monitoring system comprising the membrane according to any one of the preceding exemplary embodiments.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. While certain optional features are described as embodiments of the invention, the description is meant to encompass and specifically disclose all combinations of these embodiments unless specifically indicated otherwise or physically impossible.

The invention claimed is:

1. A composition for forming a membrane comprising from 90 to 99.5 wt %, based on the total weight of the composition, of a solvent and from 0.5 to 10 wt %, based on the total weight of the composition, of a polymer mixture, the polymer mixture comprising from 60 to 99.5 wt %, based on the total weight of the polymer mixture, of a polyurethane and from 0.5 to 40 wt %, based on the total weight of the polymer mixture, of a free hydrophilic polymer comprising a polyoxazoline,
   wherein the polyurethane comprises a backbone comprising the reaction product of a diisocyanate, a polymeric aliphatic diol, and optionally a chain extender, and
   wherein the free hydrophilic polymer is a hydrophilic polymer that is not bound to the polyurethane by covalent bonds.

2. A membrane comprising:
   a. a free hydrophilic polymer comprising a polyoxazoline, and
   b. a polyurethane, the polyurethane comprising a backbone comprising a reaction product of a diisocyanate, a polymeric aliphatic diol, and optionally a chain extender,
wherein the free hydrophilic polymer is a hydrophilic polymer that is not bound to the polyurethane by covalent bonds.

3. The membrane according to claim 2, wherein the membrane comprises from 90 to 99 wt %, based on the total weight of the membrane, of the polyurethane, and from 1.0 to 10 wt %, based on the total weight of the membrane, of the free hydrophilic polymer.

4. The membrane according to claim 2, wherein the free hydrophilic polymer comprises poly(2-methyl-2-oxazoline) or poly(2-ethyl-2-oxazoline).

5. The membrane according to claim 2, wherein the free hydrophilic polymer consists of poly(2-methyl-2-oxazoline), poly(2-ethyl-2-oxazoline), copolymers thereof, or a mixture thereof.

6. The membrane according to claim 2, wherein the free hydrophilic polymer has a number average molecular weight of at least 100,000 g/mol and at most 1,000,000 g/mol.

7. The membrane according to claim 2, wherein the polyurethane comprises an endgroup and the endgroup is present in an amount of at least 0.1 wt % and at most 3 wt %, based on the total weight of the polyurethane.

8. The membrane according to claim 2, wherein the polymeric aliphatic diol comprises a polysiloxane diol or a random or block copolymer diol comprising a polysiloxane.

9. The membrane according to claim 2, wherein the polyurethane comprises a $C_2$-$C_{16}$ fluoroalkyl or a $C_2$-$C_{16}$ fluoroalkyl ether.

10. The membrane according to claim 2, wherein the polymeric aliphatic diol comprises a polysiloxane diol, a polycarbonate diol, a poly(tetramethylene oxide) diol, or a mixture thereof.

11. The membrane according to claim 2, wherein the polymeric aliphatic diol comprises a polysiloxane diol and one or more of a polycarbonate diol and a poly(tetramethylene oxide) diol.

12. The membrane according to claim 2, wherein the polyurethane is devoid of a hydrophilic polymer moiety.

13. The membrane according to claim 2, wherein the polyurethane backbone comprises a polysiloxane and the polyurethane comprises an average of from 0.25 to 3 endgroups per molecule comprising a $C_2$-$C_{16}$ fluoroalkyl or a $C_2$-$C_{16}$ fluoroalkyl ether.

14. The composition according to claim 1, wherein the solvent comprises 40 wt % or more of tetrahydrofuran (THF), methyl-tetrahydrofuran (methyl-THF), or a mixture thereof, and methanol, ethanol, isobutanol, propanol, methyl ethyl ketone, or a mixture thereof at an amount of from 1 to 60 wt %, based on the total amount of solvent in the composition.

15. The composition according to claim 1, wherein the solvent comprises at least 40 wt % of THF, and methanol, ethanol, or a mixture thereof at an amount of from 1 to 60 wt %, based on the total amount of solvent in the composition.

16. The composition according to claim 1, wherein the solvent comprises at least 70 wt % of THF, and propanol, isobutanol, methyl-THF, or methyl ethyl ketone, or a mixture thereof, at an amount of from 1 to 30 wt %, based on the total amount of solvent in the composition.

17. The composition according to claim 1, wherein the free hydrophilic polymer is present in an amount of from 5 to 40 wt %, based on the total combined weight of the polyurethane and the free hydrophilic polymer.

18. A membrane formed from a composition comprising from 90 to 99.5 wt %, based on the total weight of the composition, of a solvent and from 0.5 to 10 wt %, based on the total weight of the composition, of a polymer mixture, the polymer mixture comprising:
   a. from 60 to 99.5 wt %, based on the total weight of the polymer mixture, of a polyurethane, and
   b. from 0.5 to 40 wt %, based on the total weight of the polymer mixture, of a free hydrophilic polymer comprising a polyoxazoline,
wherein the polyurethane comprises a backbone comprising the reaction product of a diisocyanate, a polymeric aliphatic diol, and optionally a chain extender, and
wherein the free hydrophilic polymer is a hydrophilic polymer that is not bound to the polyurethane by covalent bonds.

19. The membrane according to claim 18, wherein the membrane has a residual solvent content of less than 50 ppm after drying the membrane under nitrogen for 24 hours followed by drying in a convection oven at 50° C. for one hour.

20. A sensor comprising the membrane according to claim 2, wherein the sensor is configured to detect glucose, lactic acid, glutamate, pyruvate, choline, acetylcholine, nitric oxide, sodium, potassium, calcium, chloride, bicarbonate, urea, creatine, or dopamine in the blood stream or another bodily fluid.

\* \* \* \* \*